(12) United States Patent
Foitzik et al.

(10) Patent No.: US 10,131,340 B2
(45) Date of Patent: Nov. 20, 2018

(54) DEVICE AND METHOD FOR ASCERTAINING AT LEAST ONE VARIABLE REGARDING A STATE OF A BRAKE FLUID IN A BRAKE SYSTEM OF A VEHICLE

(71) Applicant: Robert Bosch GmbH, Stuttgart (DE)

(72) Inventors: Bertram Foitzik, Ilsfeld (DE); Dagobert Masur, Flein (DE)

(73) Assignee: ROBERT BOSCH GMBH, Stuttgart (DE)

( * ) Notice: Subject to any disclaimer, the term of this patent is extended or adjusted under 35 U.S.C. 154(b) by 396 days.

(21) Appl. No.: 14/834,667

(22) Filed: Aug. 25, 2015

(65) Prior Publication Data
US 2016/0052500 A1 Feb. 25, 2016

(30) Foreign Application Priority Data
Aug. 25, 2014 (DE) .......................... 10 2014 216 843

(51) Int. Cl.
| | |
|---|---|
| *B60T 17/22* | (2006.01) |
| *G01F 1/00* | (2006.01) |
| *G01N 11/04* | (2006.01) |
| *B60T 13/68* | (2006.01) |
| *G01F 1/36* | (2006.01) |

(52) U.S. Cl.
CPC ............ *B60T 17/22* (2013.01); *B60T 13/686* (2013.01); *B60T 17/221* (2013.01); *G01F 1/00* (2013.01); *G01N 11/04* (2013.01); *G01F 1/36* (2013.01); *G01F 1/363* (2013.01)

(58) Field of Classification Search
CPC .................................... B60T 17/22; G01F 1/00
USPC ............................................. 73/504.01, 5.014
See application file for complete search history.

(56) References Cited

FOREIGN PATENT DOCUMENTS

DE 10 2009 028 542 A1 2/2011

*Primary Examiner* — Harshad R Patel
*Assistant Examiner* — Jamel Williams
(74) *Attorney, Agent, or Firm* — Norton Rose Fulbright US LLP; Gerard Messina (57) ABSTRACT

For ascertaining at least one variable regarding a state of a brake fluid in a brake system of a vehicle, an evaluation unit is configured to determine the at least one variable by taking into account at least one pair of values of a provided or ascertained volume flow variable regarding a volume flow of at least a portion of the brake fluid through a flow resistance in the brake system and a provided or ascertained associated pressure drop variable regarding a pressure drop at the flow resistance through which the volume flow flows. For the at least one pair of values taken into account, a volume flow variable lies within a first specified limited value range and the pressure drop variable lies within a second specified limited value range.

19 Claims, 4 Drawing Sheets

DEVICE AND METHOD FOR ASCERTAINING AT LEAST ONE VARIABLE REGARDING A STATE OF A BRAKE FLUID IN A BRAKE SYSTEM OF A VEHICLE

FIELD OF THE INVENTION

The present invention relates to a device for ascertaining at least one variable regarding a state of a brake fluid in a brake system of a vehicle. The present invention also relates to a brake system for a vehicle. The present invention also relates to a method for ascertaining at least one variable regarding a state of a brake fluid in a brake system of a vehicle.

BACKGROUND

DE 10 2009 028 542 A1 describes a method and a device for controlling a brake system. When using the device or when implementing the method, a portion of the brake system is hydraulically decoupled from the remaining portion of the brake system, upon which a pressure change in the decoupled portion of the brake system resulting from a volume displacement in the decoupled portion is ascertained and evaluated for the purpose of determining a p-V characteristic curve (pressure-volume characteristic curve). Controlling the brake system is to be facilitated by way of the obtained p-V characteristic curve of the decoupled portion of the brake system.

SUMMARY

An example embodiment of the present invention is directed to a device for ascertaining at least one variable regarding a state of a brake fluid in a brake system of a vehicle. An example embodiment of the present invention is directed to a brake system for a vehicle. An example embodiment of the present invention is directed to a method for ascertaining at least one variable regarding a state of a brake fluid in a brake system of a vehicle.

The present invention facilitates a simple and reliable ascertainment of at least one variable regarding a state of a brake fluid in a brake system of a vehicle. The present invention facilitates, in particular, determining reliably and with great accuracy the effects of variables that impair the flow properties of valves/valve seats of a brake system such as, for example, viscosity, temperature, water content, aging state, and/or (chemical) composition, of the brake fluid. Knowing the flow property obtained in this manner makes it possible to optimize a dynamic performance of control signals output to the brake system. The present invention is therefore able to contribute significantly toward optimizing an operation of the brake system.

The present invention facilitates performing a regular/continual update of the at least one variable during an operation of the brake system. The regularly/continually performed update can subsequently be used for adapting the control signals output to the brake system to a changed property or a changed physical variable of the brake fluid.

In an example embodiment, the evaluation unit is able to determine, as the at least one variable and with a relatively high accuracy and a comparatively low risk of error, a viscosity, temperature, water content, aging state, and/or composition, of the brake fluid. When determining any of the listed variables, it is possible to dispense with the use of an additional sensor, which is not designed for ascertaining the volume flow variable and the associated pressure drop variable. In particular, it is possible to dispense with the use of a temperature sensor.

In an example embodiment, the evaluation unit is designed, for example, to determine the volume flow variable by taking into account at least one displacement speed of a displaceable piston, by which the respective volume flow is pressed through the flow resistance situated in the brake system, and, for the respective volume flow, to ascertain or use the pair of values from the volume flow variable and the associated pressure drop variable for determining the at least one variable only if the at least one displacement speed of the displaceable piston for producing the volume flow lies within a particular value range limited by a specified limit displacement speed. This reliably eliminates the risk that influences triggered by an excessively fast displacement of the displaceable piston result in an inaccuracy/faultiness of the at least one variable to be determined.

The limit volume flow variable preferably corresponds to a limit volume flow that is smaller than a maximum volume flow through the flow resistance occurring during an operation of the brake system. It is likewise preferred that the limit pressure drop variable corresponds to a limit pressure drop that is smaller than a maximum pressure drop occurring at the flow resistance during an operation of the brake system. Furthermore, the limit displacement speed is preferably smaller than a maximum displacement speed of the displaceable piston triggered during an operation of the brake system.

In an example embodiment, the evaluation unit is designed to determine a first coefficient $k_1$ from a first pair of values of the ascertained pairs of values and a second pair of values of the ascertained pairs of values that is ascertained after the first pair of values, as follows:

$$k_1 = \frac{\ln\frac{\Delta p_1}{\Delta p_2}}{\ln\frac{Q_1}{Q_2}}$$

where $Q_1$ is a first volume flow as a first volume flow variable of the first pair of values, $\Delta p_1$ is a first pressure drop as a first pressure drop variable of the first pair of values, $Q_2$ is a second volume flow as a second volume flow variable of the second pair of values and $\Delta p_2$ is a second pressure drop as a second pressure drop variable of the second pair of values.

In addition, in an example embodiment, the evaluation unit is configured to determine a second coefficient $k_2$, as follows:

$$k_2 = \frac{\Delta p_2}{Q_2^{k_1}}$$

In this case, the evaluation unit is optionally designed to determine the at least one variable by taking into account the second coefficient $k_2$ or an average value of multiple second coefficients $k_2$. This ensures a relatively accurate and advantageously error-free determination of the at least one variable.

An example embodiment of the present invention is directed to a brake system for a vehicle including the described device.

An example embodiment of the present invention is directed to a method for ascertaining at least one variable regarding a state of a brake fluid in a brake system of a vehicle.

Additional features and advantages of the present invention are elucidated below with reference to the figures.

DETAILED DESCRIPTION

According to an example embodiment of the present invention, a method is provided that facilitates ascertaining at least one variable that represents a state of a brake fluid in a brake system of a vehicle/motor vehicle. The at least one variable can be for example a physical variable and/or a property of the brake fluid present in the respective brake system. The feasibility of the method described below is not limited to a specific material for the examined brake fluid, is not limited to a brake system type of the brake system comprising the brake fluid, and is not limited to a vehicle type/motor vehicle type of the vehicle/motor vehicle equipped with the brake system.

Figure 1A:
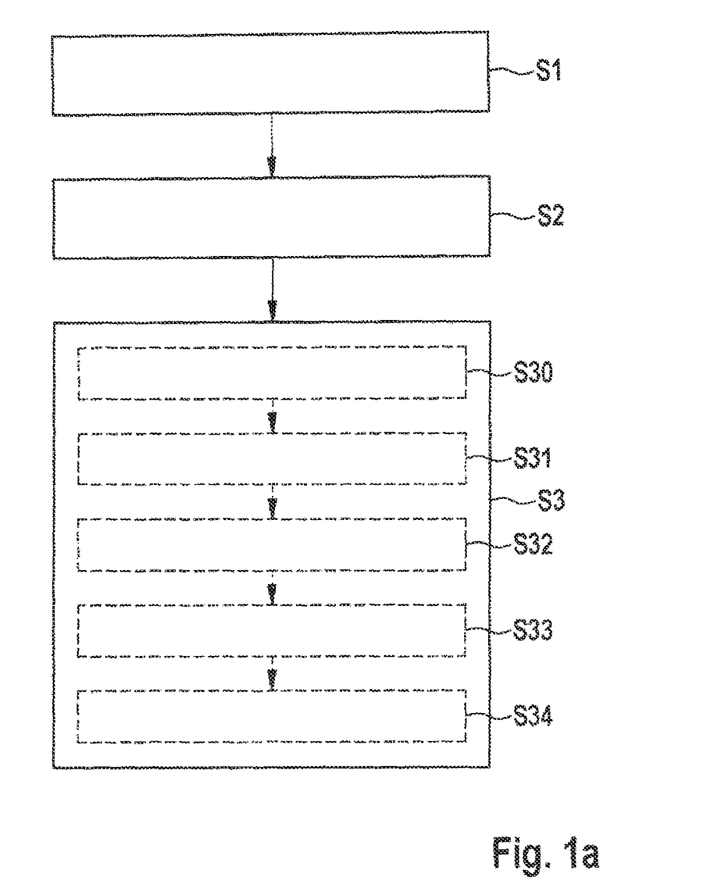
FIGS. 1a-1f include a flowchart and coordinate systems corresponding to a method for ascertaining at least one variable regarding a state of a brake fluid in a brake system of a vehicle, according to an example embodiment of the present invention.

Referring to FIG. 1a, in a method step S1 that is performed at least once, a volume flow variable is ascertained regarding a volume flow Q of at least a portion of the brake fluid that is pressed through a flow resistance situated in the brake system. The at least one volume flow variable ascertained in this manner can be for example volume flow Q or a physical variable corresponding to volume flow Q. (Examples for a brake system component usable as a flow resistance will be described below.) If the respective volume flow Q is pressed through the flow resistance situated in the brake system in that a displaceable piston is displaced at at least one displacement speed $v_p$, then it is possible to determine volume flow Q in a simple manner by taking into account a piston geometry of the displaceable piston and the at least one displacement speed $v_p$ of the displaceable piston (when triggering volume flow Q).

In addition, step S2 is performed at least once in the method. In method step S2, a pressure drop variable is determined regarding a pressure drop $\Delta p$ occurring at the flow resistance through which volume flow Q flows. The respective pressure drop variable can be pressure drop $\Delta p$ or a physical variable corresponding to pressure drop $\Delta p$. A particularly practicable possibility for ascertaining pressure drop $\Delta p$ at the flow resistance through which the volume flow flows will be explained below. Method steps S1 and S2 can be performed in any order or at least partly simultaneously.

Figure 1B:
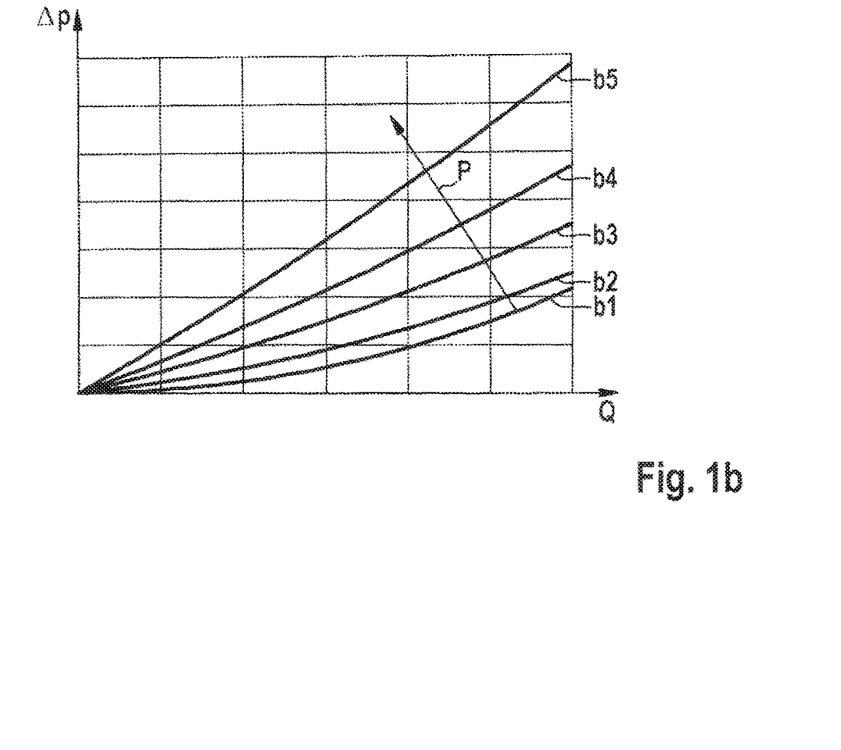

FIG. 1b shows a coordinate system, the abscissa of which indicates a volume flow Q channeled through a flow resistance, and the ordinate of which indicates a pressure drop $\Delta p$ (a pressure difference). Each of the graphs b1 through b5 plotted in the coordinate system of FIG. 1b is an approximation of measured values obtained when using a brake fluid having a specific viscosity v, where brake fluids having different viscosities v were used to determine the measured values of the different graphs. (An increase of viscosities v of the brake fluids is represented by an arrow P.) For each of graphs b1 through b5, the equation (Eq. 1) can be ascertained as approximation, where $$\Delta p = k_2 Q^{k_1} \quad \text{(Eq. 1)}$$

Equation (Eq. 1) thus describes in a good approximation a relationship between a volume flow Q flowing through a flow resistance and a pressure drop $\Delta p$ occurring at the flow resistance, a first coefficient $k_1$ and a second coefficient $k_2$ resulting from a curve approximation. The values Q and $\Delta p$ ascertained by the at least one execution of method steps S1 and S2 are thus reliably suited to determine the at least one variable.

In a method step S3, the at least one variable is determined by taking into account at least one pair of values of the volume flow variable and the associated pressure drop variable. To determine the at least one variable, however, the at least one pair of values of the volume flow variable and the associated pressure drop variable is only evaluated if, for the respective pair of values, the volume flow variable lies within a first value range W1 limited by a specified limit volume flow variable and the pressure drop variable lies within a second value range W2 limited by a specified limit pressure drop variable. In a determination of the at least one variable performed in method step S3, no pair of values is evaluated whose volume flow variable lies outside of the first value range W1 limited by the specified limit volume flow variable and/or whose pressure drop variable lies outside the second value range W2 limited by the specified limit pressure drop variable.

Preferably, in method step S3, the variable $k_2$ proportional to viscosity v is determined as the at least one variable. It is likewise possible, however, to determine a viscosity v, a temperature, a water content, an aging state, and/or a (chemical) composition, of the brake fluid as the at least one variable. An explanation is provided below why method step S3 is particularly advantageously suited for determining at least one of these listed variables.

Figure 1C:
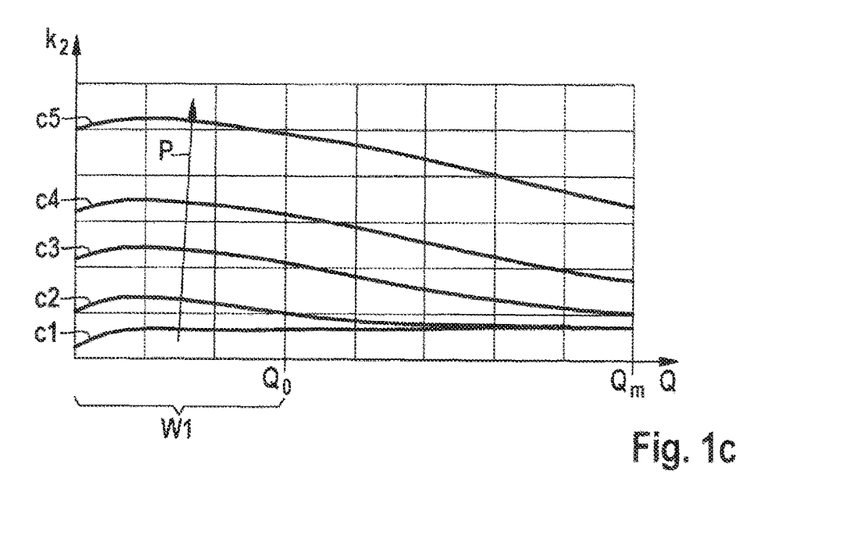

FIG. 1c shows a coordinate system, the abscissa of which represents a volume flow Q flowing through a flow resistance and the ordinate of which represents associated values of the second coefficient $k_2$. Graphs c1 through c5 respectively correspond to a second coefficient $k_2$ in different brake fluids having different viscosities v. (The increase of viscosities v of the brake fluids is represented by an arrow P.)

It can be seen that the second coefficient $k_2$ for a volume flow Q under a specified limit volume flow $Q_0$ (as the limit volume flow variable) depends only on viscosity v of the respective brake fluid. (Accordingly, it is also possible to derive a dependence of second coefficient $k_2$ on the temperature, water content, aging state, and/or (chemical) composition, of the brake fluid for a volume flow Q under the specified limit volume flow $Q_0$.) The limitation of the at least one pair of values evaluated in method step S3 to pairs of values whose volume flow variable lies within the first value range W1 limited by the specified limit volume flow variable thus ensures an accurate and (nearly) error-free determination of the at least one variable.

The limit volume flow variable corresponds to a limit volume flow $Q_0$, which is smaller than a maximum volume flow $Q_m$ flowing through the flow resistance during an operation of the brake system. (The volume flow variables/volume flows Q in the first value range W1 are normally smaller than the limit volume flow variable/the limit volume flow $Q_0$.) In the example of FIG. 1c, limit volume flow $Q_0$ is smaller than maximum volume flow $Q_m$, preferably smaller than three quarters of maximum volume flow $Q_m$, in particular smaller than half of maximum volume flow $Q_m$. If desired, limit volume flow $Q_0$ can also be smaller than a quarter of maximum volume flow $Q_m$.

Figure 1D:
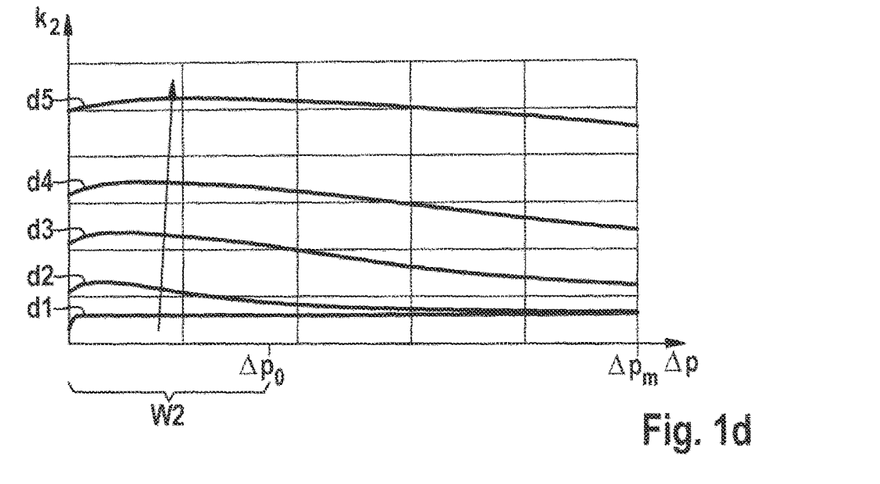

FIG. 1d shows a coordinate system, the abscissa of which represents a pressure drop $\Delta p$ (as pressure difference) occurring at a flow resistance that has a flow passing through it and the ordinate of which represents associated values of the second coefficient $k_2$. Graphs d1 through d5 correspond to a second coefficient $k_2$ in different brake fluids having different viscosities v. (The increase of viscosities v of the brake fluids is represented by arrow P.) The example of FIG. 1d also shows clearly that as long as pressure drop $\Delta p$ is smaller than specified limit pressure drop $\Delta p_0$ (as limit pressure drop variable), second coefficient $k_2$ depends only on viscosity v of the respective brake fluid. (A corresponding dependence of second coefficient $k_2$ on the temperature, water content, aging state, and/or (chemical) composition, of the brake fluid may also be derived for a pressure drop $\Delta p$ under the specified limit pressure drop $\Delta p_0$.)

The limit pressure drop variable also corresponds to a limit pressure drop $\Delta p_0$, which is smaller than a maximum pressure drop $\Delta p_m$ occurring at the flow resistance during the operation of the brake system. (Usually, the pressure drop variables/pressure drops in the second value range W2 are smaller than the limit pressure drop variable/the limit pressure drop $\Delta p_0$.) In the example of FIG. 1d, limit pressure drop $\Delta p_0$ is smaller than maximum pressure drop $\Delta p_m$, preferably smaller than three quarters of maximum pressure drop $\Delta p_m$, in particular smaller than half of maximum pressure drop $\Delta p_m$. If desired, limit pressure drop $\Delta p_0$ can also be smaller than a quarter of maximum pressure drop $\Delta p_m$.

Method step S3 is therefore particularly well suited to determine, as the at least one variable, a variable that is proportional to the viscosity v of the brake fluid, such as in particular variable $k_2$, with high accuracy and a low error rate. Method step S3 is likewise suited to determine, as the at least one variable, the viscosity v, temperature, aging state, water content, and/or (chemical) composition, of the brake fluid with high accuracy and a low error rate.

If the respective volume flow Q is pressed through the flow resistance by displacing the displaceable piston at the at least one displacement speed $v_p$, the pair of values of the volume flow variable and the associated pressure drop variable is preferably ascertained/used to determine the at least one variable for the respective volume flow Q only if the at least one displacement speed $v_p$ of the displaceable piston lies within a third value range W3 limited by a specified limit displacement speed $v_0$. In this way, it is possible reliably to avoid the risk of inaccuracies/errors in the at least one variable determined in method step S3 (due to turbulences in the brake fluid displaced at an excessively high displacement speed $v_p$).

Figure 1E:
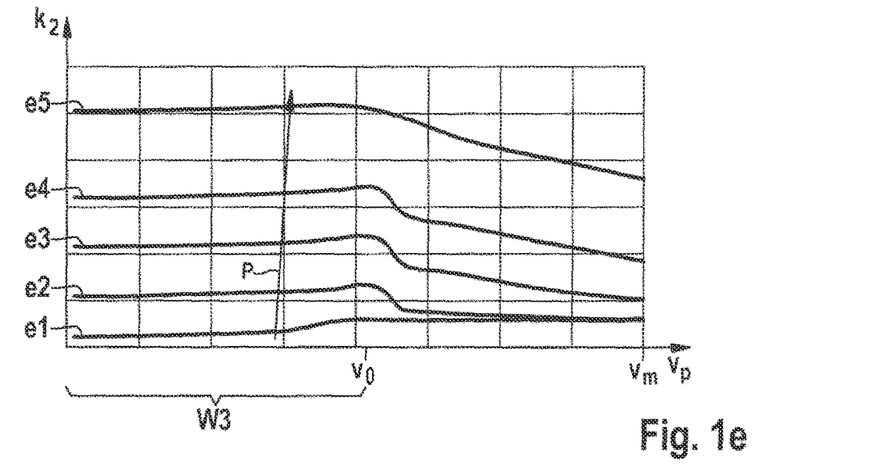

FIG. 1e shows a coordinate system, the abscissa of which represents a displacement speed $v_p$ of the displaceable piston and the ordinate of which represents associated values of the second coefficient $k_2$. Graphs e1 through e5 correspond to a second coefficient $k_2$ in different brake fluids having different viscosities v. (The increase of viscosities v of the brake fluids is represented by arrow P.) In graphs e1 through e5, second coefficient $k_2$ for a displacement speed $v_p$ of the displaceable piston under the limit displacement speed $v_0$ depends only on the viscosity v of the used brake fluid. A corresponding dependence of second coefficient $k_2$ on the temperature, water content, aging state, and/or (chemical) composition, of the brake fluid can also be derived for a displacement speed $v_p$ of the displaceable piston under the limit displacement speed $v_0$.

The limit displacement speed $v_0$ is preferably also smaller than a maximum displacement speed $v_m$ of the displaceable piston triggered during an operation of the brake system. (Displacement speeds $v_p$ of the third value range W3 are normally smaller than limit displacement speed $v_0$.) In the example of FIG. 1e, limit displacement speed $v_0$ is smaller than three quarters of maximum displacement speed $v_m$. If desired, limit displacement speed $v_0$ can also be smaller than half of maximum displacement speed $v_m$, in particular smaller than a quarter of maximum displacement speed $v_m$.

Ensuring that in method step S3 only pairs of values are evaluated for which the volume flow variable lies within the first value range W1, and the pressure drop variable lies within the second value range W2 (and, if applicable, the at least one displacement speed $v_p$ of the displaceable piston lies within the third value range W3), makes it possible for the at least one variable to be reliably determined by taking into account the first coefficient $k_1$ and the second coefficient $k_2$. Optionally, in a sub-step S30 of method step S3, at least one pair of values can be filtered out of the pairs of values ascertained in method steps S1 and S2, for which it is true at least that its volume flow variable lies outside of the first value range W1, that its pressure drop variable lies outside of the second value range W2, or (if applicable) that the at least one displacement speed $v_p$ of the displaceable piston lies outside of the third value range W3. The at least one pair of values that was filtered out is subsequently not used for determining the at least one variable. An execution of sub-step S30 can alternatively be omitted, however. For example, after detecting a volume variable outside of first value range W1, the method can already be aborted prior to carrying out method step S2. Likewise, after detecting a pressure drop variable outside of second value range W2, the method can already be aborted prior to carrying out method step S1. Accordingly, the method can already be aborted prior to carrying out at least one of method steps S1 and S2 as soon as a displacement speed $v_p$ of the displaceable piston outside of third value range W3 is ascertained.

In the specific embodiment of FIGS. 1a through 1f, first a sub-step S31 is carried out for determining the at least one variable. In sub-step S31, first coefficient $k_1$ is determined from a first pair of values of the ascertained pairs of values and a second pair of values of the ascertained pairs of values that is ascertained after the first pair of values in accordance with equation (Eq. 2), where:

$$k_1 = \frac{\ln\frac{\Delta p_1}{\Delta p_2}}{\ln\frac{Q_1}{Q_2}} \tag{Eq. 2}$$

where $Q_1$ is a first volume flow as the first volume flow variable of the first pair of values, $\Delta p_1$ is a first pressure drop as the first pressure drop variable of the first pair of values, $Q_2$ is a second volume flow as the second volume flow variable of the second pair of values and $\Delta p_2$ is a second pressure drop as the second pressure drop variable of the second pair of values. First coefficient $k_1$ may thus be calculated from respectively two successively ascertained pairs of values that are suitable for the evaluation.

Subsequently, the second coefficient $k_2$ can be determined in a sub-step S32 in accordance with equation (Eq. 3), where:

$$k_2 = \frac{\Delta p_2}{Q_2^{k_1}} \quad \text{(Eq. 3)}$$

In an optional sub-step S33, it is possible to determine an average value of multiple second coefficients $k_2$ (which can be calculated by repeated execution of sub-steps S31 and S32 for different successive pairs of values). If necessary, in a sub-step S34, the at least one variable can then be determined by taking into account the average value of multiple second coefficients $k_2$. An execution of sub-step S33 can alternatively also be omitted, however. In this case, the at least one variable is determined in sub-step S34 by taking into account (only) the second coefficient $k_2$.

To determine the at least one variable in sub-step S34, it is also possible to use at least one stored characteristic curve k. For example, viscosity v of the brake fluid can be determined as the at least one variable by taking into account the second coefficient $k_2$/the average value of multiple second coefficients $k_2$ and a corresponding characteristic curve k. Instead of a viscosity-dependent characteristic curve of the second coefficient $k_2$, it is also possible to use, for determining the at least one variable, a temperature-dependent characteristic curve of the second coefficient $k_2$, a characteristic curve k of the second coefficient $k_2$ dependent on a water content in the brake fluid, and/or a characteristic curve of the second coefficient $k_2$ dependent on an aging state of the brake fluid. Such characteristic curves can also be evaluated for the advantageous determination of the at least one variable.

Figure 1F:
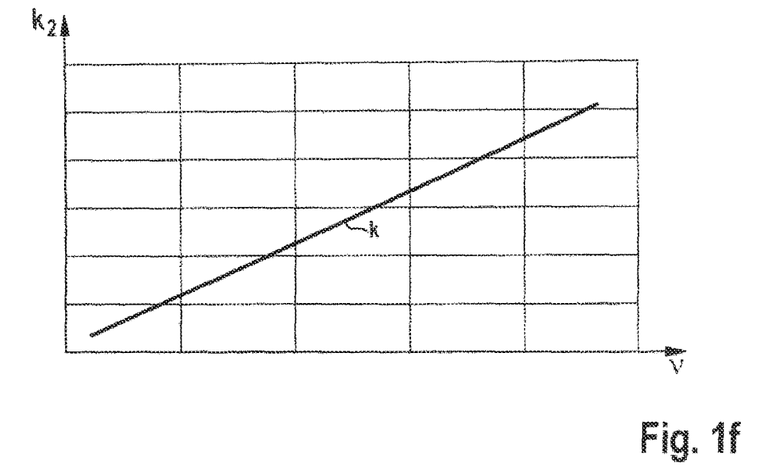

FIG. 1f shows a coordinate system, the abscissa of which represents a viscosity v and the ordinate of which represents associated values of the second coefficient $k_2$. Since a characteristic curve k represented in Figure if indicates a linear relation between the second coefficient $k_2$ and viscosity v, it is easy to execute sub-step S34. Characteristic curve k represented in FIG. 1f, however, is merely one example for a relation between the at least one variable and second coefficient $k_2$/average value of multiple second coefficients $k_2$ that is suitable for carrying out sub-step S34.

In an optional additional method step, the at least one variable determined in method step S3, such as in particular variable $k_2$, can be evaluated in order to derive additional variables. For example, viscosity v, temperature, aging state, water content, and/or the (chemical) composition of the brake fluid can be derived from the at least one variable, in particular from variable $k_2$. Such a method step is optional, however. A figurative representation of such a method step is omitted here.

An advantage of the method described here is that it is not necessary to know any single property, such as e.g., the temperature of the brake fluid, the aging state of the brake fluid, the water content of the brake fluid, and/or the (chemical) composition of the brake fluid, in order to make use of the method to determine the at least one variable such as in particular the variable $k_2$ or the viscosity v of the brake fluid.

Figure 2:
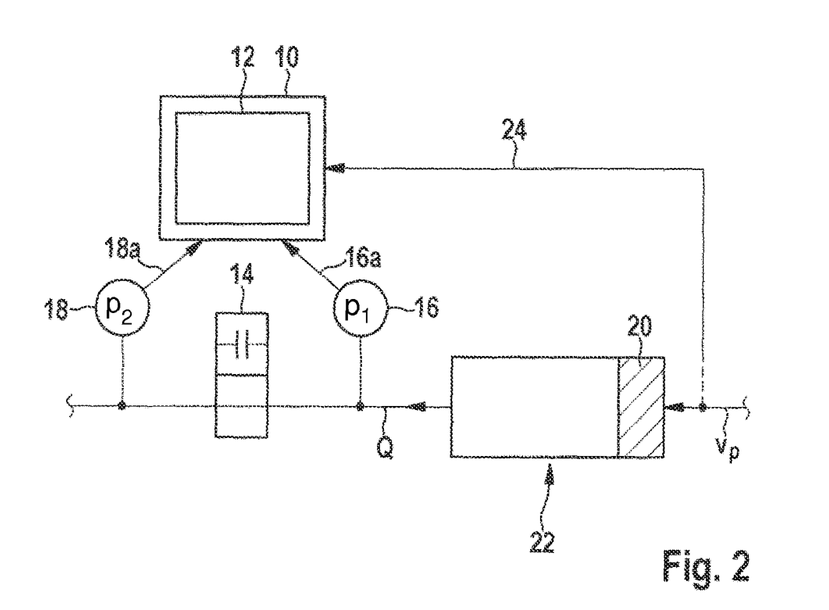
FIG. 2 is a schematic representation of a device for ascertaining at least one variable regarding a state of a brake fluid in a brake system of a vehicle, according to an example embodiment of the present invention.

FIG. 2 shows a schematic representation of a device 10 for ascertaining at least one variable regarding a state of a brake fluid in a brake system of a vehicle.

The device 10 shown schematically in FIG. 2 includes an evaluation unit 12, which is designed to determine the at least one variable. This occurs by taking into account at least one pair of values of a provided or ascertained volume flow variable and a provided or ascertained associated pressure drop variable. The volume flow variable is to be understood as a variable regarding a volume flow Q of at least one portion of the brake fluid through a flow resistance 14 situated in the brake system. Accordingly, the pressure drop variable is a variable regarding a pressure drop Δp occurring at flow resistance 14 through which volume flow Q flows. For the at least one pair of values taken into account/evaluated (when determining the at least one variable), it is respectively the case that the volume flow variable lies within a first value range limited by a specified limit volume flow variable and the pressure drop variable lies within a second value range limited by a specified limit pressure drop variable.

Flow resistance 14 can be, for example, a hydraulic component situated in the brake system, at which the brake fluid is (slightly) throttled. In the specific embodiment of FIG. 2, flow resistance 14 is a solenoid valve 14. As an alternative to a solenoid valve 14, however, flow resistance 14 can be a throttle for example.

A first pressure sensor 16 is connected on an input of flow resistance 14, through which volume flow Q flows, in such a way that, by way of first pressure sensor 16, it is possible to determine a first pressure $p_1$ prevailing (directly) at the input of flow resistance 14, or a variable corresponding to the first pressure $p_1$. Additionally, a second pressure sensor 18 is connected on an output of flow resistance 14, through which volume flow Q flows, in such a way that, by way of second pressure sensor 18, it is possible to determine a second pressure $p_2$ prevailing (directly) at the output of flow resistance 14, or a variable corresponding to the second pressure $p_2$. The connection of pressure sensors 16 and 18 on flow resistance 14 is preferably realized in such a way that a difference between the first pressure $p_1$ measured using first pressure sensor 16 and the second pressure $p_2$ measured using second pressure sensor 18 corresponds to the pressure drop Δp occurring at flow resistance 14.

Evaluation unit 12 can be designed for example to ascertain the pressure drop variable/the pressure drop Δp by taking into account a first pressure signal 16a provided by first pressure sensor 16 and a second pressure signal 18a provided by second pressure sensor 18. It is also possible, however, for the pressure drop variable/the pressure drop Δp to be ascertained by another interposed element (which can be part of the device or can be separate from the device) from signals 16a and 18a and provided to evaluation unit 12.

In the brake system shown only partially in FIG. 2, volume flow Q through flow resistance 14 situated in the brake system is triggered in that a displaceable piston 20 is displaced at at least one displacement speed $v_p$. Displaceable piston 20 can be situated for example in a (motorized) piston-cylinder unit 22, in particular in a plunger. Additional possible components of the brake system interacting with device 10 are not shown in FIG. 2.

Evaluation unit 12 can be designed in particular to determine the volume flow variable/the volume flow Q by taking into account the at least one displacement speed $v_p$ of displaceable piston 20 (by which the respective volume flow Q is pressed through flow resistance 14 situated in the brake system). This is possible for example by a continuous measurement of the displacement speed $v_p$ of displaceable piston 20 using a sensor element (not shown) (which can be part of the device or can be separate from the device). Likewise, however, a signal 24 of the at least one displacement speed $v_p$ of displaceable piston 20, or of a corresponding variable, can be output to evaluation unit 12 by the motor displacing the displaceable piston 20. Furthermore, device 10 can also be designed to control the motor (not shown) of displaceable piston 20. In this case, information about the at least one displacement speed $v_p$ of displaceable piston 20 is already available in device 10 without measurement.

In an example embodiment, if the respective volume flow Q is pressed through flow resistance 14 situated in the brake system by displacing displaceable piston 20, evaluation unit 12 is preferably designed to ascertain or use the pair of values of the volume flow variable and the associated pressure drop variable to determine the at least one variable for the respective volume flow Q only if the at least one displacement speed $v_p$ of the displaceable piston 20 for effecting the volume flow Q lies within a third value range limited by a specified limit displacement speed.

It is possible to determine variable $k_2$, which is proportional to a viscosity of the brake fluid, as the at least one variable using evaluation unit 12. Alternatively or additionally, using evaluation unit 12, it is also possible to determine the viscosity, temperature, water content, aging state, and/or a composition, of the brake fluid as the at least one variable. For this purpose, evaluation unit 12 can perform the method steps described above. Another description of the method steps executable by evaluation unit 12 is here omitted, however.

Since the at least one variable can be ascertained by using a very simple model, the algorithms to be applied for this purpose can already be stored in a cost-effective evaluation unit 12 that requires little installation space. Device 10 equipped with evaluation unit 12 is therefore inexpensive, light, and requires little installation space.

Device 10 is able to do without the use of a temperature sensor. For the use of device 10, it is also not necessary for a brake fluid specification to be known.

The at least one variable $k_2$, which is proportional to the viscosity of the brake fluid and which is determined by device 10 or the above-described method, or the viscosity of the brake fluid, can be used to estimate ram pressure effects on valves of the respective brake system. In this manner, a regulation of pressures "behind" the valves of the brake system can be considerably improved. A wheel-pressure regulation for example can be optimized via an adjustable admission pressure. Furthermore, the at least one ascertained variable, specifically the viscosity, can be used to define setpoint flow rates through the respective valves, in particular for setpoint flow rate specifications when supplying fluid at low pressures. The viscosity can specifically also be used for estimating ram pressure effects when detecting braking requests in a simulator system.

For a later operation of the brake system by taking into account the at least one determined variable, it is advantageous that the flow resistance 14 used for ascertaining the at least one variable be located in the same hydraulic unit as the other hydraulic components of the brake system. Consequently, the same environmental conditions and the same brake fluid properties prevail at flow resistance 14 as at the other hydraulic components of the brake system. The at least one variable determined by way of device 10 or the above-described method can thus be used reliably to control the other hydraulic components of the brake system.

The advantages described above are also ensured in a brake system for a vehicle/motor vehicle including device 10.

What is claims is:
1. A device comprising:
a sensor arrangement; and
processing circuitry communicatively coupled to the sensor arrangement, wherein the processing circuitry is configured to determine at least one variable regarding a state of a brake fluid in a brake system of a vehicle by taking into account at least one pair of values obtained based on signals of the sensor arrangement, the at least one pair of values including:
a value that (a) is of a volume flow variable regarding a volume flow of at least one portion of the brake fluid through a flow resistance situated in the brake system, and (b) lies within a predefined limiting first value range, and
a value that (a) is of a pressure drop variable regarding a pressure drop occurring at the flow resistance through which the volume flow flows, and (b) lies within a predefined limiting second value range; and
an arrangement for controlling the brake system in accordance with the determined at least one variable.

2. The device of claim 1, wherein the at least one variable includes at least one of a viscosity of the brake fluid, a temperature of the brake fluid, a water content of the brake fluid, an aging state of the brake fluid, and a composition of the brake fluid.

3. The device of claim 1, wherein the processing circuitry is configured to:
determine the volume flow variable by taking into account at least one displacement speed of a displaceable piston arranged for pressing the volume flow through the flow resistance situated in the brake system; and
for the volume flow, ascertain or use the pair of values for determining the at least one variable only if the at least one displacement speed lies within a predefined limiting third value range.

4. The device of claim 1, wherein at least one of:
the first value range corresponds to a limit volume flow that is smaller than a maximum volume flow through the flow resistance occurring during an operation of the brake system; and
the second value range corresponds to a limit pressure drop that is smaller than a maximum pressure drop occurring at the flow resistance during an operation of the brake system.

5. The device of claim 4, wherein:
the processing circuitry is configured to:
determine the volume flow variable by taking into account at least one displacement speed of a displaceable piston arranged for pressing the volume flow through the flow resistance situated in the brake system;
for the volume flow, ascertain or use the pair of values only for determining the at least one variable if the at least one displacement speed lies within a predefined limiting third value range; and
a highest displacement speed value of the third value range is less than a maximum displacement speed of the displaceable piston triggered during an operation of the brake system.

6. The device of claim 1, wherein:
the processing circuitry is configured to:
determine the volume flow variable by taking into account at least one displacement speed of a displaceable piston arranged for pressing the volume flow through the flow resistance situated in the brake system;
for the volume flow, ascertain or use the pair of values only for determining the at least one variable if the at least one displacement speed lies within a predefined limiting third value range; and a highest displacement speed value of the third value range is less than a maximum displacement speed of the displaceable piston triggered during an operation of the brake system.

7. The device of claim 1, wherein:
the at least one pair of values includes a first pair of values and a second pair of values ascertained after ascertainment of the first pair of values;
the processing circuitry is configured to determine a first coefficient $k_1$ from the first and second pairs of values;

$$k_1 = \frac{\ln\frac{\Delta p_1}{\Delta p_2}}{\ln\frac{Q_1}{Q_2}};$$

$Q_1$ is a first volume flow value used as the first volume flow variable of the first pair of values;
$\Delta p_1$ is a first pressure drop value used as the first pressure drop variable of the first pair of values;
$Q_2$ is a second volume flow value used as the second volume flow variable of the second pair of values; and
$\Delta p_2$ is a second pressure drop value used as the second pressure drop variable of the second pair of values.

8. The device of claim 7, wherein the processing circuitry is configured to determine a second coefficient $k_2$ as $$k_2 = \frac{\Delta p_2}{Q_2^{k_1}}.$$

9. The device of claim 8, wherein the processing circuitry is configured to determine the at least one variable by taking into account the second coefficient $k_2$ or an average value of multiple second coefficients $k_2$.

10. A brake system for a vehicle comprising:
a device that includes:
a sensor arrangement; and
processing circuitry communicatively coupled to the sensor arrangement, wherein the processing circuitry is configured to determine at least one variable regarding a state of a brake fluid in the brake system by taking into account at least one pair of values obtained based on signals of the sensor arrangement, the at least one pair of values including:
a value that (a) is of a volume flow variable regarding a volume flow of at least one portion of the brake fluid through a flow resistance situated in the brake system, and (b) lies within a predefined limiting first value range; and
a value that (a) is of a pressure drop variable regarding a pressure drop occurring at the flow resistance through which the volume flow flows, and (b) lies within a predefined limiting second value range; and
an arrangement for controlling the brake system in accordance with the determined at least one variable.

11. A method comprising:
ascertaining at least once, by processing circuitry and using sensor signals, a volume flow variable regarding a volume flow of at least a portion of brake fluid that is pressed through a flow resistance situated in a brake system;
ascertaining at least once, by the processing circuitry and using sensor signals, a pressure drop variable regarding a pressure drop occurring at the flow resistance through which the volume flow flows;
determining at least one variable regarding a state of the brake fluid in the brake system by taking into account at least one pair of values that includes:
a value that (a) is of the volume flow variable, and (b) lies within a predefined limiting first value range; and
a value that (a) is of the pressure drop variable, and (b) lies within a predefined limiting second value range; and
controlling the brake system in accordance with the determined at least one variable.

12. The method of claim 11, wherein the at least one variable includes at least one of a viscosity of the brake fluid, a temperature of the brake fluid, a water content of the brake fluid, an aging state of the brake fluid, and a composition of the brake fluid.

13. The method of claim 11, wherein the volume flow is pressed through the flow resistance by displacing a displaceable piston at at least one displacement speed, and the pair of values is used for determining the at least one variable only if the at least one displacement speed lies within a predefined limiting third value range.

14. The method of claim 11, wherein at least one of:
the first value range corresponds to a limit volume flow that is smaller than a maximum volume flow through the flow resistance occurring during an operation of the brake system; and
the second value range corresponds to a limit pressure drop that is smaller than a maximum pressure drop occurring at the flow resistance during an operation of the brake system.

15. The method of claim 14, wherein:
the volume flow is pressed through the flow resistance by displacing a displaceable piston at at least one displacement speed;
the pair of values is used for determining the at least one variable only if the at least one displacement speed lies within a predefined limiting third value range; and
a highest displacement speed value of the third value range is less than a maximum displacement speed of the displaceable piston triggered during an operation of the brake system.

16. The method of claim 11, wherein:
the volume flow is pressed through the flow resistance by displacing a displaceable piston at at least one displacement speed;
the pair of values is used for determining the at least one variable only if the at least one displacement speed lies within a predefined limiting third value range; and
a highest displacement speed value of the third value range is less than a maximum displacement speed of the displaceable piston triggered during an operation of the brake system.

17. The method of claim 11, wherein:
the at least one pair of values includes a first pair of values and a second pair of values ascertained after ascertainment of the first pair of values;
the method further comprises determining a first coefficient $k_1$ from the first and second pairs of values:

$$k_1 = \frac{\ln\frac{\Delta p_1}{\Delta p_2}}{\ln\frac{Q_1}{Q_2}};$$

$Q_1$ is a first volume flow value used as the first volume flow variable of the first pair of values;

$\Delta p_1$ is a first pressure drop value used as the first pressure drop variable of the first pair of values;

$Q_2$ is a second volume flow value used as the second volume flow variable of the second pair of values; and $\Delta p_2$ is a second pressure drop value used as the second pressure drop variable of the second pair of values.

18. The method of claim 17, further comprising, for determining the at least one variable, determining a second coefficient $k_2$ as $$k_2 = \frac{\Delta p_2}{Q_2^{k_1}}.$$

19. The method of claim 18, wherein the at least one variable is determined by taking into account the second coefficient $k_2$ or an average value of multiple second coefficients $k_2$.

* * * * *